United States Patent [19]

Makino et al.

[11] 4,021,728

[45] May 3, 1977

[54] MAGNETIC FIELD SENSING APPARATUS FOR SENSING THE PROXIMITY OF A MEMBER HAVING HIGH MAGNETIC PERMEABILITY WITHOUT REQUIRING AN EXTERNAL FIELD SOURCE

[75] Inventors: Yoshimi Makino, Fujisawa; Hiroyuki Ookubo, Chiba, both of Japan

[73] Assignee: Sony Corporation, Tokyo, Japan

[22] Filed: Dec. 22, 1975

[21] Appl. No.: 642,997

[30] Foreign Application Priority Data

Dec. 29, 1974  Japan ............................ 50-2141

[52] U.S. Cl. ............................ 324/41; 324/46; 338/32 R; 324/34 D
[51] Int. Cl.$^2$ ........................... G01R 33/12
[58] Field of Search ............. 324/34 D, 34 PS, 41, 324/43 R, 45, 46; 338/32 R, 32 H; 323/94 H; 360/113

[56] References Cited

UNITED STATES PATENTS

| | | | |
|---|---|---|---|
| 2,997,648 | 8/1961 | Bozorth | 324/46 |
| 3,405,355 | 10/1968 | Hebbert | 324/46 |
| 3,493,694 | 2/1970 | Hunt | 324/46 |
| 3,546,579 | 12/1970 | Paul et al. | 324/46 |
| 3,613,000 | 10/1971 | Weir et al. | 324/46 |
| 3,777,273 | 12/1973 | Baba et al. | 324/34 PS |
| 3,928,836 | 12/1975 | Makino et al. | 324/46 |

OTHER PUBLICATIONS

Hill, Y. M.; Velocity Sensing with a Hall Probe, IBM Tech. Bul. vol. 6, No. 6, Nov., 1963, p. 54.
Bate et al., Magnetoresistive Read Heads, IBM Tech. Bul., vol. 17, No. 4, Sept., 1974, pp. 967–968.

Primary Examiner—Robert J. Corcoran
Attorney, Agent, or Firm—Lewis H. Eslinger; Alvin Sinderbrand

[57] ABSTRACT

Apparatus is provided for producing an output signal upon sensing the proximity of a member having relatively high magnetic permeability. The apparatus includes a magnetoresistive element which is comprised of an insulating substrate upon which first and second ferromagnetic strips are provided. The ferromagnetic strips define first and second main current conducting paths which are respectively perpendicular to each other. The strips are connected in series to define a junction therebetween from which an output signal is derived. Current supply terminals are provided for furnishing an energizing current to the magnetoresistive element, which energizing current flows in a direction from one to the other of the current supply terminals. A bias magnetic field is provided in a direction perpendicular to one of the main current conducting paths and which is sensed by the element. A portion of this bias field is received by a member having a relatively high magnetic permeability which is proximate the element, thereby altering the distribution of the received portion of the bias field to produce a composite field which can be considered a vector formed of the bias field and the field attributed to the permeable material. The composite field is a function of the spacing between the element and the member and the longitudinal positioning of the member with respect to the element. This composite magnetic field is sensed by the element, whereby an output signal is produced from the junction in the element as a function of the relative positions of leading and trailing edges of the member with respect to the magnetoresistive element.

17 Claims, 24 Drawing Figures

MAGNETIC FIELD SENSING APPARATUS FOR SENSING THE PROXIMITY OF A MEMBER HAVING HIGH MAGNETIC PERMEABILITY WITHOUT REQUIRING AN EXTERNAL FIELD SOURCE

BACKGROUND OF THE INVENTION

This invention relates to apparatus for producing an output signal upon sensing a magnetic field and, in particular, to such apparatus which is capable of sensing the proximity of a member having material of high magnetic permeability.

In many applications it is desired to produce a switching function as a function of a mechanical device, but without the use of mechanical contacts which must be engaged by and thus physically closed by the mechanical device. Such an operation generally can be achieved by a contactless switch. That is, depending upon the position of the mechanical device in question, a switching function, such as the actuation of an electronic switching element, can be performed. Generally, diverse types of contactless switches are known. Among these are photoelectric devices, electro-static devices and magnetic-sensitive devices, all of which can be used to perform a switching function without actual physical engagement of mechanical contacts.

A typical magnetic-sensitive switching element which has been used heretofore is the well-known magnetic head which is generally used as an electro-magnetic transducer for recording and playback operations in the tape recording art. When used as a switch, an electric output signal is produced as a function of a magnet which is juxtaposed to the magnetic head. Consequently, when the relative position of the magnetic head and a magnetic pole is charged, this change in position produces the electric output signal. Hence, depending upon the particular application thereof, the magnetic head can be used to produce various switching functions, accordingly.

However, the use of the magnetic head as a switch suffers from various disadvantages. One disadvantage is the relatively large structure which must be used. The magnetic head requires an electromagnetic coil element, a suitable supporting core and a bias signal oscillator in order for the head to detect the presence and proximity of an external magnetic field. Furthermore, for those applications wherein the magnetic head is to be used as a contactless limiter switch, a highly sensitive output cannot be achieved unless the head is very closely spaced adjacent the source of magnetic field, that is, the magnet. Such very close spacing severely limits the applications of this head to contactless switching arrangements. Hence, the magnetic head does not enjoy diverse usage, nor has it been overwhelmingly successful in many commercial applications.

Many of the foregoing disadvantages attending the use of the magnetic head as a switching element have been overcome by the use of a magnetoresistive element, as disclosed in copending U.S. application Ser. No. 597,007, filed July 18, 1975, by the inventors of the present invention. As described therein, the magnetoresistive element is comprised of an insulating substrate having perpendicular, series-connected, current conducting ferromagnetic strips thereon. When this element senses a magnetic field produced by a generator magnet which is proximate thereto, an output signal is produced which is a function of the relative positions of the leading and trailing edges of the generator magnet with respect to the element. Although this device is satisfactory for many applications, there are some instances wherein it is desirable to use the magnetoresistive element to sense the proximity of a member which is not itself a magnet. But if the member to be sensed is not a magnet, the necessary magnetic field which must be detected cannot be produced.

OBJECTS OF THE INVENTION

Therefore, it is an object of the present invention to provide improved magnetic sensing apparatus for producing an output signal in response to the sensing of the proximity of a magnetically permeable member.

It is another object of this invention to provide an improved magnetically actuated switching device which does not suffer from the disadvantages attending prior art devices.

Yet another object of this invention is to provide a magnetic field detector including a magnetoresistive element capable of producing an output signal in response to a magnetic field, but which does not require a field source externally of the detector.

Yet another object of this invention is to provide a contactless switch including a magnetoresistive element.

A still further object of the present invention is to provide a miniature, highly sensitive magnetic field sensing device which can be used as a contactless switch.

An additional object of this invention is to provide apparatus for providing an indication of the relative position of a member formed of a highly permeable material.

A further object of the present invention is to provide apparatus for detecting the movement and direction of movement of a member.

Another object of this invention is to provide apparatus for producing an encoded representation of the angular position of a rotary element.

Still another object of the present invention is to provide a magnetic-sensitive card reader for an information card.

Various other objects and advantages of the present invention will become apparent from the ensuing detailed description and the novel features will be particularly pointed out in the appended claims.

SUMMARY OF THE INVENTION

The present invention proceeds upon the fact that the magnetoresistive detector of the type disclosed in copending application Ser. No. 597,007, produces an output signal which is a function of the strength and direction of a magnetic field which passes therethrough. In the copending application the source of this magnetic field is the generator magnet, whose relative position is sensed. In the present invention a bias magnet is provided to establish a magnetic field which is substantially perpendicular to the general direction of current supplied to the magnetoresistive element. This field through the element due to the bias magnet is altered when a material of high magnetic permeability is proximate the field; primarily because the flux from the bias magnet can pass through the permeable material. The direction of the composite field, which can be considered to be a vector formed of the field attributed to the bias magnet and the field attributed to the permeable material, is a function of the relative position of the permeable material with respect to the magnetoresistive element. The magnetoresistive element produces an output signal as a function of this composite magnetic field.

Apparatus is provided for producing an output signal upon sensing the proximity of a member comprised of material having a relatively high magnetic permeability comprising a magnetoresistive element which has an insulating substrate and first and second ferromagnetic strips on the substrate for providing first and second main current conducting paths which are perpendicular to each other, the strips being connected in series to define a junction therebetween; a bias magnet for providing a magnetic field in a direction perpendicular to one of the current conducting paths, the magnetic field passing through the magnetoresistive element; and a member comprised of material having a relatively high magnetic permeability has a surface disposed in a plane spaced from the magnetoresistive element to alter the magnetic field through the magnetoresistive element, so that an output signal is derived from the junction defined by the ferromagnetic strips which is a function of the relative positions of the leading and trailing edges of the member with respect to the magnetoresistive element.

BRIEF DESCRIPTION OF THE DRAWINGS

The following detailed description will best be understood in conjunction with the accompanying drawings in which:

FIGS. 12 and 13 show how the present invention can be used to detect motion and motion related conditions such as length, speed, direction of movement, and the like;

FIGS. 14, 15 and 16 show how the present invention can be used to detect the rotation of a rotary member, which finds application as a rotary speed detector, a shaft encoder, and the like;

DETAILED DESCRIPTION OF CERTAIN ONES OF THE PREFERRED EMBODIMENTS

Figure 1:
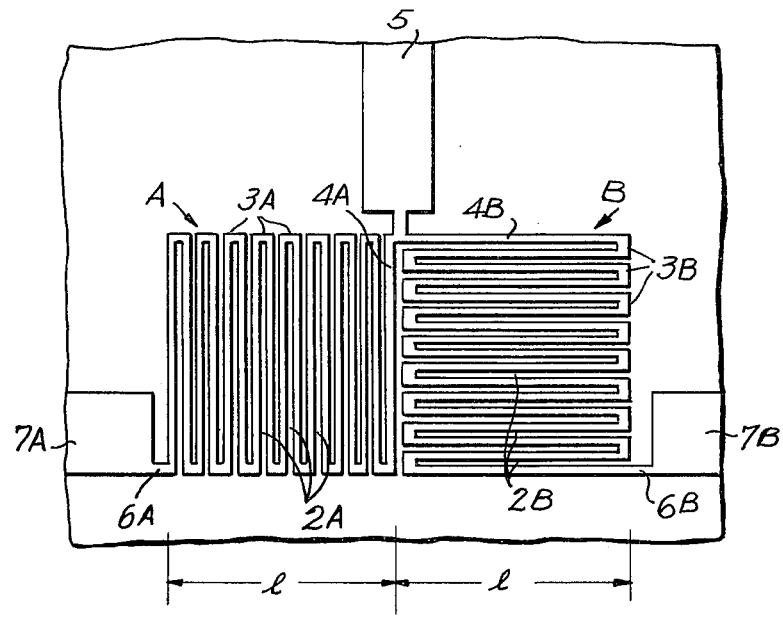
FIG. 1 is a plan view of a magnetoresistive element which can be used in one embodiment of the invention.

Referring now to the drawings wherein like reference numerals are used throughout and, in particular, to FIG. 1, there is illustrated a schematic representation of a magnetoresistive element 1 which can be used with the present invention. A thin film of ferromagnetic material is deposited, as by a conventional vacuum evaporation technique, for example, on an insulating substrate to a depth of approximately 600 to 1,000 A. Typical examples of the substrate are a glass slide, a photographic dry plate, or the like. Other suitable materials can be used. Then, the thin film is etched so as to form the ferromagnetic strips A and B in zig-zag or serpentine configuration, as shown, or in strips, together with the terminals 5, 7A and 7B. The ferromagnetic strips A and B comprise a plurality of main current conducting paths 2A and 2B and associated connecting portions 3A and 3B, respectively. The main current paths 2A and 2B are substantially perpendicular to each other. As viewed in FIG. 1, the strips A are capable of conducting current predominantly in the vertical direction and the strips B are capable of conducting current predominantly in the horizontal direction. Of course, as is realized, other mutually perpendicular current conducting directions can be employed. The last path 4A of the main current path 2A is connected in series to the first path 4B of the main current path 2B. The connecting junction defined by the last path 4A and the first path 4B is connected to the terminal 5. The terminals 7A and 7B are adapted to serve as current supply terminals to the magnetoresistive element and are connected to the paths 2A and 2B by portions 6A and 6B, respectively.

The magnetoresistive element 1 is disclosed in further detail in copending application Ser. No. 487,282, filed July 10, 1974, now U.S. Pat. No. 3,928,836, issued Dec. 23, 1975 and assigned to the same assignee of the present invention. Also, the use of this magnetoresistive element to detect the direction of a magnetic field is disclosed in copending application Ser. No. 597,818, filed July 21, 1975. As described in the latter application, it is preferable to use the magnetoresistive element 1 in a magnetic field having sufficient intensity to saturate the ferromagnetic strips A and B so as to obtain a self-limiting effect at the output signal, whereby the output signal is substantially insensitive to changes in field intensity.

Figure 2:
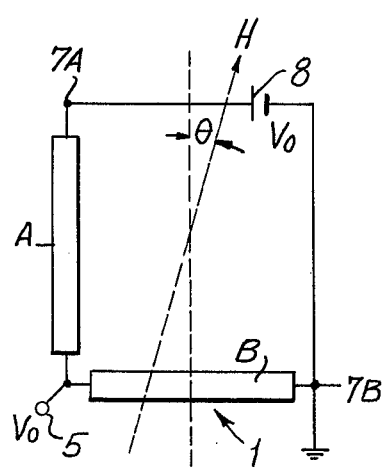
FIG. 2 is a schematic view illustrating the principles of operation of a magnetoresistive element as applied to this invention.

Turning to FIG. 2, the strips A and B are schematically represented as being connected electrically to each other in series. The current supply terminals 7A and 7B are connected to the opposed ends of the strips A and B, and the output terminal 5 is connected to the junction defined by the series connection of the strips. A power source 8 is connected between the current supply terminals 7A and 7B. One current supply terminal 7B is connected to a reference potential, such as ground. The resultant magnetoresistive element forms a sensing circuit 1 for detecting magnetic fields.

Let it be assumed that a magnetic field H having an intensity sufficient to saturate the strips A and B is applied to the strips at an angle $\theta$ relative to the longitudinal direction of the strip A. Generally, the resistance of a saturated ferromagnetic material is anisotropic. That is, the resistance of such a material is greater in the direction of magnetization than in the direction perpendicular thereto. Accordingly, resistances $\rho_A$ and $\rho_B$ of the strips A and B can be represented by the Voight-Thomson formula:

$$\rho_A(\theta) = \rho_\perp \sin^2\theta + \rho_\parallel \cos^2\theta \qquad (1)$$

$$\rho_B(\theta) = \rho_\perp \cos^2\theta + \rho_\parallel \sin^2\theta \qquad (2)$$

where $\rho_\perp$ is the resistance of the ferromagnetic strip A or B when saturated with a magnetic field perpendicular to the longitudinal direction of the strip, and $\rho_\parallel$ is the resistance of the ferromagnetic strip when saturated with a magnetic field parallel with the longitudinal direction of the strip.

Figure 4:
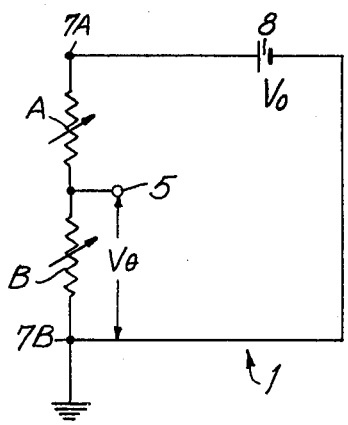
FIG. 4 is an equivalent circuit diagram of FIG. 2.

FIG. 4 represents an equivalent circuit of the magnetoresistive element shown in FIG. 2. A voltage $V(\theta)$ at the output terminal 5 will be derived by voltage division and is represented by $$V(\theta) = \frac{\rho_B(\theta)}{\rho_A(\theta) + \rho_B(\theta)} \cdot V_o \qquad (3)$$

where $V_0$ is the voltage of the power source 8.

By substitution of equations (1) and (2) into equation (3), and by rearranging terms, $$V(\theta) = \frac{V_o}{2} - \frac{\Delta\rho \cos 2\theta}{2(\rho_\parallel + \rho_\perp)} \cdot V_o \qquad (4)$$

where $\Delta\rho = \rho_\parallel - \rho_\perp$.

In equation (4), the first term represents a constant voltage $V_s$ which is a function of the power source ($V_s = V_o/2$), and the second term represents a change or deviation from the constant voltage, attributed to the influence of the magnetic field H. This change in the output voltage is represented as $\Delta V(\theta)$. If the resistance of the ferromagnetic strip A or B in the absence of the field H is expressed as $\rho_o$, and if $2\rho_o = \rho_\parallel + \rho_\perp$, then $\Delta V(\theta)$ can be rewritten as $$\Delta V(\theta) = -\frac{\Delta\rho}{4\rho_o} \cdot \cos 2\theta \cdot V_o \qquad (5)$$

It is appreciated, from equation (5), that $\Delta V(\theta)$ is a maximum positive or negative value, that is, the absolute value of the change of the output voltage is maximum, at angles $\theta$ of 0°, 90°, 180° and 270°, where $\cos 2\theta$ is ±1.

Figure 3:
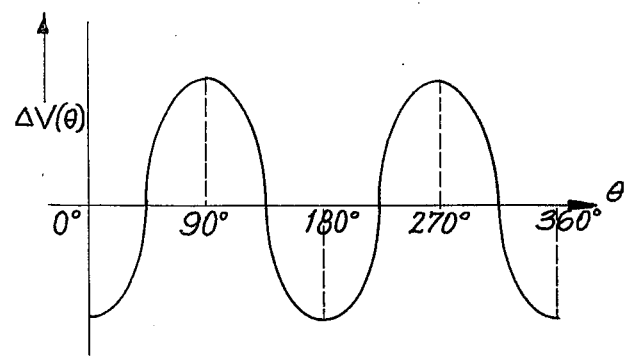
FIG. 3 is a graph illustrating the relationship between a change in the output signal of the magnetoresistive element and the direction of a magnetic field applied thereto.

Equation (4) can be graphically depicted as shown in FIG. 3. As is apparent, the output $V(\theta)$ of the magnetoresistive element is equal to $V_o/2$ when the magnetic field H is applied to the strips at an angle $\theta = 45°$. That is, $\Delta V(\theta) = 0$ because at $\theta = 45°$, $\cos 2\theta = 0$. Also, the output voltage $V(\theta)$ is minimum and maximum at angles $\theta = 0°$ and 90°, respectively.

Figure 5:
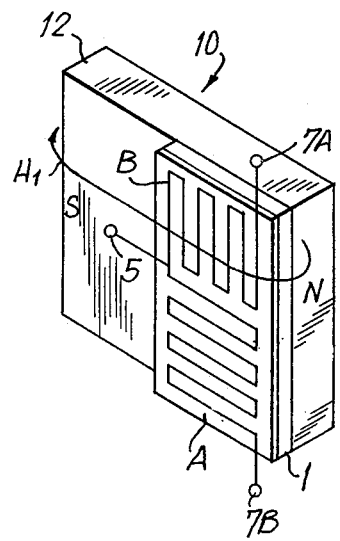
FIG. 5 shows one embodiment of the magnetoresistive element in combination with a bias magnet, which can be used to sense the proximity of magnetically permeable material.

The manner in which the magnetic field is supplied to the magnetoresistive element depicted in FIG. 1 and mathematically described hereinabove is shown in FIG. 5. The magnetoresistive element 1 is provided with a magnetic field $H_1$ which is seen to be substantially perpendicular to the general current path extending from the terminal 7A to the terminal 7B. That is, the direction of the field $H_1$ is perpendicular to one of the main current paths, e.g., the strips B. Preferably, the source of this magnetic field $H_1$ is a bias magnet 12 upon which the magnetoresistive element 1 is mounted, as by conventional bonding materials. As one example, a silicon bond or rubber sheet can be used to join the element 1 to the bias magnet 12. The resultant combination formed thereby hereinafter is designated by the reference numeral 10.

The longitudinal dimension of the bias magnet 12 is greater than the corresponding dimension of the element 1 so that the magnet extends beyond the boundaries established by the element, as shown. To obtain the magnetic field $H_1$ in the illustrated direction, the bias magnet is magnetized in the direction of its longitudinal dimension. If the lines of flux are assumed to extend from the north pole (N) to the south pole (S) of the bias magnet 12, then such lines (and thus the magnetic field $H_1$) will pass through the element 1 parallel to the substrate.

Figure 6:
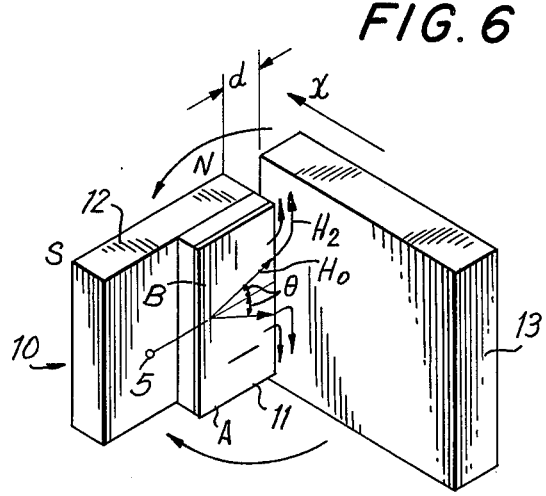
FIG. 6 is a schematic representation of how the combination shown in FIG. 5 is used to produce output signals as a function of the magnetic field passing therethrough.

If material having a relatively high magnetic permeability is disposed within the vicinity of the combination 10 such that the flux from the bias magnet is intercepted by the material, the flux will pass through the material and will significantly influence the net direction of the magnetic field which passes through the magnetoresistive element. This phenomenon is illustrated in FIG. 6 wherein a member 13 formed of material having a relatively high magnetic permeability, such as soft iron, is proximate the combination 10. The magnetic field generated by the bias magnet 12 is received by the member 13 resulting in a magnetic field $H_2$ in the member. Thus a path for the magnetic flux is established from the north pole (N) of the bias magnet, through at least a portion of the member 13 and then through the ambient (such as air) to the south pole (S) of the bias magnet. If the plane of the member 13 is substantially perpendicular to the plane of the bias magnet 12 (and thus perpendicular to the field $H_1$), then the field $H_2$ will be substantially perpendicular to the field $H_1$. Consequently, the resultant field $H_o$ which now passes through the magnetoresistive element has a component $H_1$ and a component $H_2$ which are vectorially combined as the resultant $H_0$. This resultant field $H_0$ exhibits an angle $\theta$ with respect to the $H_1$ component. That is, the direction of the resultant field is angularly displaced from the direction of the bias field which exists in the absence of the member 13. The resultant field $H_0$ and its direction $\theta$ through the magnetoresistive element is a function of the proximity and permeability of the member 13, as well as the distance $d$ between the member and the magnetoresistive element.

Let it be assumed that the member 13 is movable in the direction $X$ and that the leftmost edge and the rightmost edge of the member are assumed, in this instance, to be the leading and trailing edges, respectively. Then, when the member is moved in the $x$ direction, the magnetoresistive element produces a signal at the output terminal 5 which is a function of the relative positions of the leading and trailing edges of the member 13 with respect to the magnetoresistive element.

This output signal is in accordance with equations (4) and (5) above.

Figure 7:
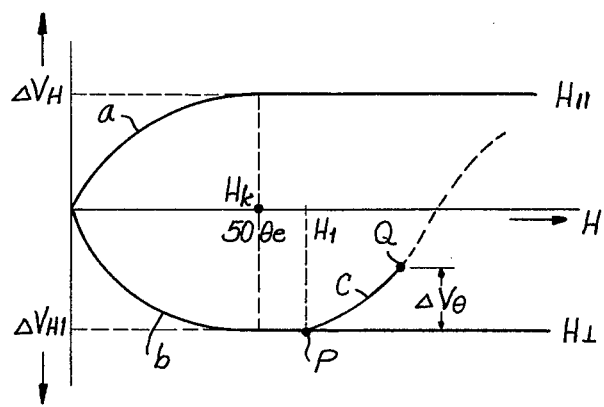
FIG. 7 is a graphical representation of the relation between the output signal produced by the magnetoresistive element and the composite magnetic field passing therethrough.

The relationship between the output signal produced by the magnetoresistive element and the magnetic field which is detected thereby is graphically depicted in FIG. 7. The point $H_k$ is the intensity of the field which is sufficient to saturate the ferromagnetic strips of the magnetoresistive element. In one example, this field intensity is equal to 50 Oe. The upper curve $a$ represents the change in the dynamic range of the output signal attributed solely to the field $H_2$ which is parallel to the general current supply path extending between the terminals 7A and 7B. The lower curve $b$ represents the change in the dynamic range of the output signal due solely to the field $H_1$ which is perpendicular to the general current supply path. If it is initially assumed that the member 13 is quite far from the combination 10, then the field $H_2$ is negligible compared to the perpendicular field $H_1$ generated by the bias magnet. Hence, the composite field vector $H_0$ will have an angle of $\theta = 0°$. If the field $H_1$ is sufficient to saturate the magnetoresistive element, the output voltage $\Delta V_{H1}$ will be as indicated at the point P of the curve in FIG. 7.

Now, as the member 13 is moved in the $+x$ direction, as depicted in FIG. 6, until the leading edge of the member is aligned with the magnetoresistive element, the change $\Delta V_\theta$ in the output signal will proceed along the curve C toward the point Q. The curve C is seen to resemble and asymptote beyond the point Q and, theoretically, would continue as depicted by the broken line if the field $H_2$ were capable of exceeding the field $H_1$. This, of course, does not occur because the field $H_2$ is induced in the member 13 by the field $H_1$.

Figure 8:
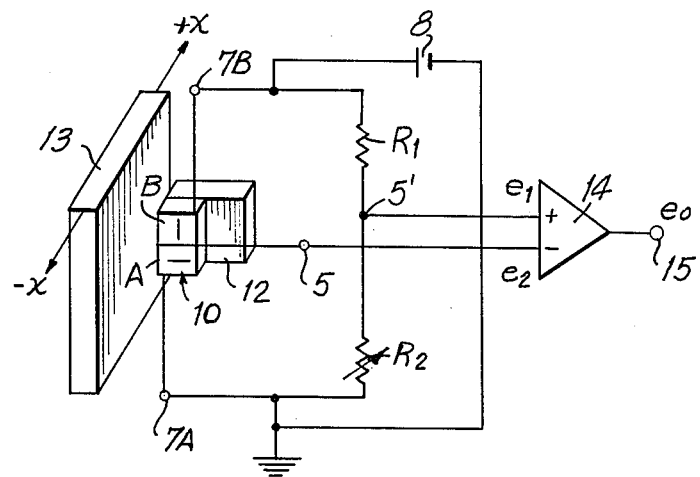
FIG. 8 is a schematic diagram showing how the output signal produced by the magnetoresistive element is processed to produce a further output signal.

Referring now to FIG. 8, a schematic circuit diagram is shown whereby an output signal $e_o$ is produced when the combination 10 is used as a detector to sense the linear movement of the member 13. Series-connected resistors $R_1$ and $R_2$ are coupled to the current supply terminals 7A and 7B of the magnetoresistive element 1 to thereby form a bridge circuit having bridge output terminals 5 and 5', respectively. This bridge circuit is energized by the power supply 8 which supplies a bias voltage $V_o$.

The bridge output terminals 5 and 5' are coupled to the input terminals of a differential amplifier 14, the output terminal of which is connected to the circuit output 15 from which the output signal $e_o$ is derived. The differential amplifier 14 is conventional and may comprise an operational amplifier having a positive input terminal connected to the bridge output terminal 5' and a negative input terminal connected to the bridge output terminal 5. Of course, if desired, these input terminal connections to the differential amplifier can be reversed.

Balance of the illustrated bridge circuit is achieved by adjusting the resistor $R_2$ which, accordingly, may comprise a potentiometer, a rheostat, or the like.

Let is be assumed that the magnetoresistive element is capable of producing an output signal which is a function of the positional relation between the member 13 and the detector 10. This positionally related output signal can be represented as $V(x)$. This signal $V(x)$ is analogous to the signal $\Delta V(\theta)$ of equation (5) above. Accordingly, it is seen that the output signal $e_2$ applied to the output terminal 5 of the magnetoresistive element can be expressed as: $e_2 = \frac{1}{2}V_o + V(x)$. The output signal $e_1$ appearing at the bridge output terminal 5' is recognized as being equal to $e_1 = \frac{1}{2}V_o$.

The differential amplifier 14 operates to subtract the signal $e_2$ from the signal $e_1$ and to suitably amplify this difference signal. Hence, if the differential amplifier 14 is assumed to have a voltage gain $\alpha$, then the output signal supplied to the terminal 15 is seen to be equal to: $e_o = \alpha(e_1 - e_2) = \alpha V(x)$. Thus, the output signal $e_o$ produced by the illustrated circuit is a direct representation of the positional relation between the detector 10 and the member 13. Relative movement therebetween results in a corresponding change in the output signal $e_o$. As will soon be seen, in many applications it is preferred that the detector 10 remain stationary.

The circuit shown in FIG. 8 to produce the output signal $e_o$ is merely illustrative; and various modifications and alternatives can be used. For example, feedback circuits can be provided with the differential amplifier to establish desired signal gain.

Figure 9A:
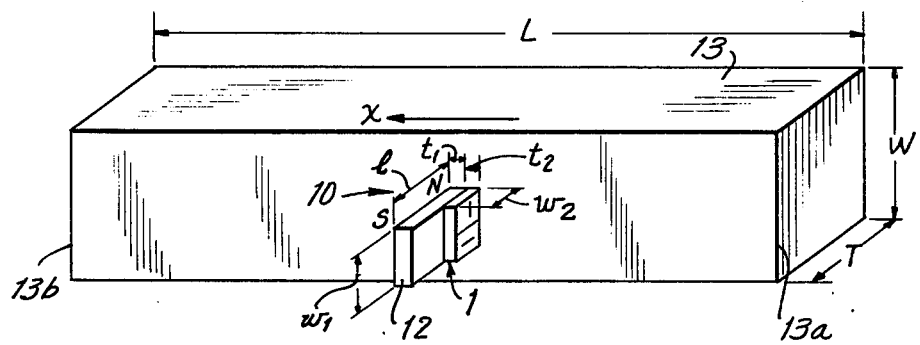
FIGS. 9A–9B show how output signals are derived from the apparatus of the present invention.
Figure 9B:
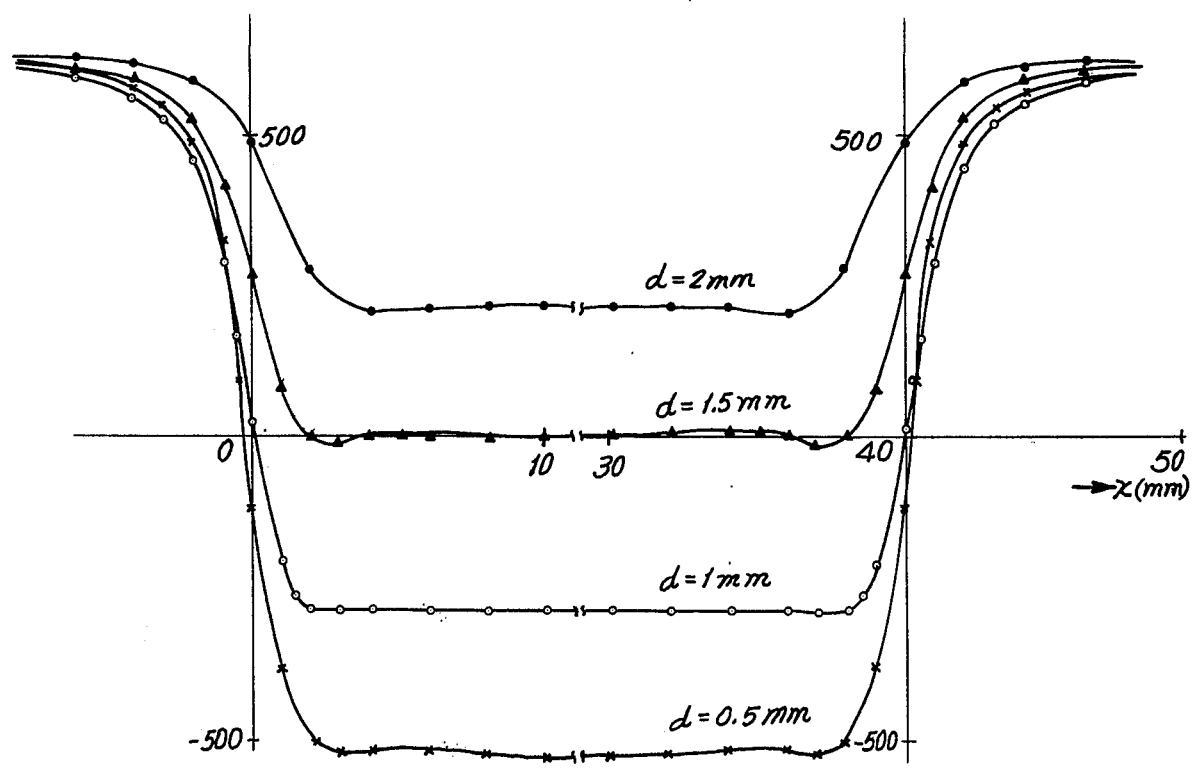

Reference now is made to FIGS. 9A and 9B which show the relationship between the output signal $e_o$ produced by the embodiment of FIG. 8 and the position of the member 13 with respect to the detector 10. In FIGS. 9A and 9B, it will be assumed that the member 13 is dimensioned so as to have a length L in the $x$ direction, a width W and a thickness T. Also, it will be assumed that the member 13 is of soft iron and its surface which is closest to the detector 10 is disposed in a plane which is spaced from the detector by the distance $d$. It will be assumed further that the bias magnet is formed of a CuNiFe alloy having a length $l$, a height $w$, and a thickness $t$, while the magnetoresistive element has a length $w_2$ and the thickness of the substract is $t_2$.

The output signal $e_o$ is represented as shown in FIG. 9B for the following parameters:

$l = 3$mm
$L = 40$ mm
$W = 6$mm
$T = 6$mm
$W_1 = 2$mm
$w_2 = 1$mm
$t_1 = 0.5$mm
$t_2 = 0.7$ mm
$d = 2$mm, 1.5mm, 1mm, 0.5mm

As shown, the bias magnet is magnetized in the direction of its length $l$ and it is assumed, in this embodiment, that the N-pole face is closest to the member 13 and the S-pole face is on the opposite end of the bias magnet. Hence, the magnetic field $H_1$ is seen to emanate from the N-pole face and is directed toward the S-pole face. The major component of this field is perpendicular to the general current supply path to the magnetoresistive element and is parallel to the substrate.

Now, let it be assumed that, initially, the member 13, although spaced from the detector 10 by the distance $d$, is very far to the right from the detector. Thus, the distance $x$ can be considered to be infinite. At this distance, the field component $H_2$ is substantially equal to zero. Hence, the angle $\theta$ is zero and the component $V(x)$ may be assumed to be zero. The output signal from the magnetoresistive element is at the point P of FIG. 7 if the element is saturated. If the member 13 is moved closer to the detector 10 in the $x$ direction, some of the flux produced by the bias magnet soon will be intercepted by the member to thereby result in the field component $H_2$. As the member 13 is moved still closer to the detector 10, the field $H_2$ increases and the angle $\theta$ due to the vector addition of the bias field $H_1$ and the field $H_2$ also increases. This causes the output signal $e_o$ (assumed to be of negative polarity in the embodiment shown in FIG. 8) to increase in absolute magnitude.

In FIG. 9B, the abscissa represents length and the origin is established for the case when the leading edge 13b of the member 13 is aligned at the site of the detector 10. Further movement of the member in the x direction causes the field $H_2$ to correspondingly increase until a point is reached at which no further flux will be intercepted by the member regardless of even further movement thereof. At this point, the field $H_2$ is substantially constant even though the member 13 continues to move in the x direction. The output signal $e_o$ produced when the field $H_2$ is constant is between +200mV and −500mV, depending upon the distance d between the member 13 and the detector 10. However, as is seen, the shapes of the different curves which are provided for the different distances d are substantially similar.

As the member continues to move in the x direction, some of the flux generated by the bias magnet and which previously had been intercepted by the member no longer will be so intercepted. This reduces the magnitude of the field $H_2$, resulting in a change in the output signal $e_o$, as shown. The influence on the output signal due to the field component $H_2$ will continue to decrease, even beyond the point at which the trailing edge 13a of the member passes beyond the site of the detector 10 (indicated at the 40mm mark of the abscissa in FIG. 9B); until the field component $H_2$ is reduced substantially to zero. The output signal $e_o$ then will be substantially equal for the positioning of the member 13 very far to the left of the detector 10 as for the initially assumed positioning of the member vary far to the right of the detector.

It is appreciated that the output signal $e_o$ having the curves depicted in FIG. 9B can be used as an indication of the proximity of the member 13 to the detector 10. Furthermore, these illustrated characteristic curves can be used as a switching function in a contactless switch.

The graphical representations in FIG. 9B indicate that the maximum peak value of the change in the output signal $e_o$ exhibits a relatively negative polarity. However, since this output signal $e_o$ is produced by the differential amplifier shown in FIG. 8, which, in turn, is supplied with the output signals $e_1$ and $e_2$ produced by the bridge circuit, it is recognized that the maximum peak value of the output signal $e_o$ can exhibit the opposite polarity (e.g. relatively positive polarity) if the differential amplifier input terminals to which the bridge circuit output signals are supplied are interchanged. That is, with respect to the circuit of FIG. 8, if the bridge output signal $e_1$ is supplied to the differential amplifier negative input terminal, and if the bridge output signal $e_2$ is supplied to the positive input terminal, then the differential amplifier output signal $e_o$ shown in FIG. 9B will be inverted.

Figure 10A:
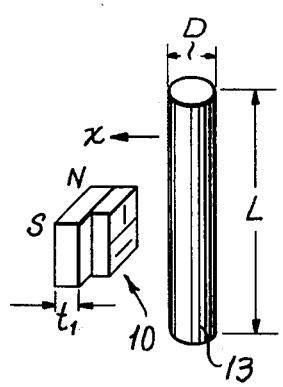
FIGS. 10A–10B show another arrangement wherein an output signal is produced as a function of the proximity of a magnetically permeable material.
Figure 10B:
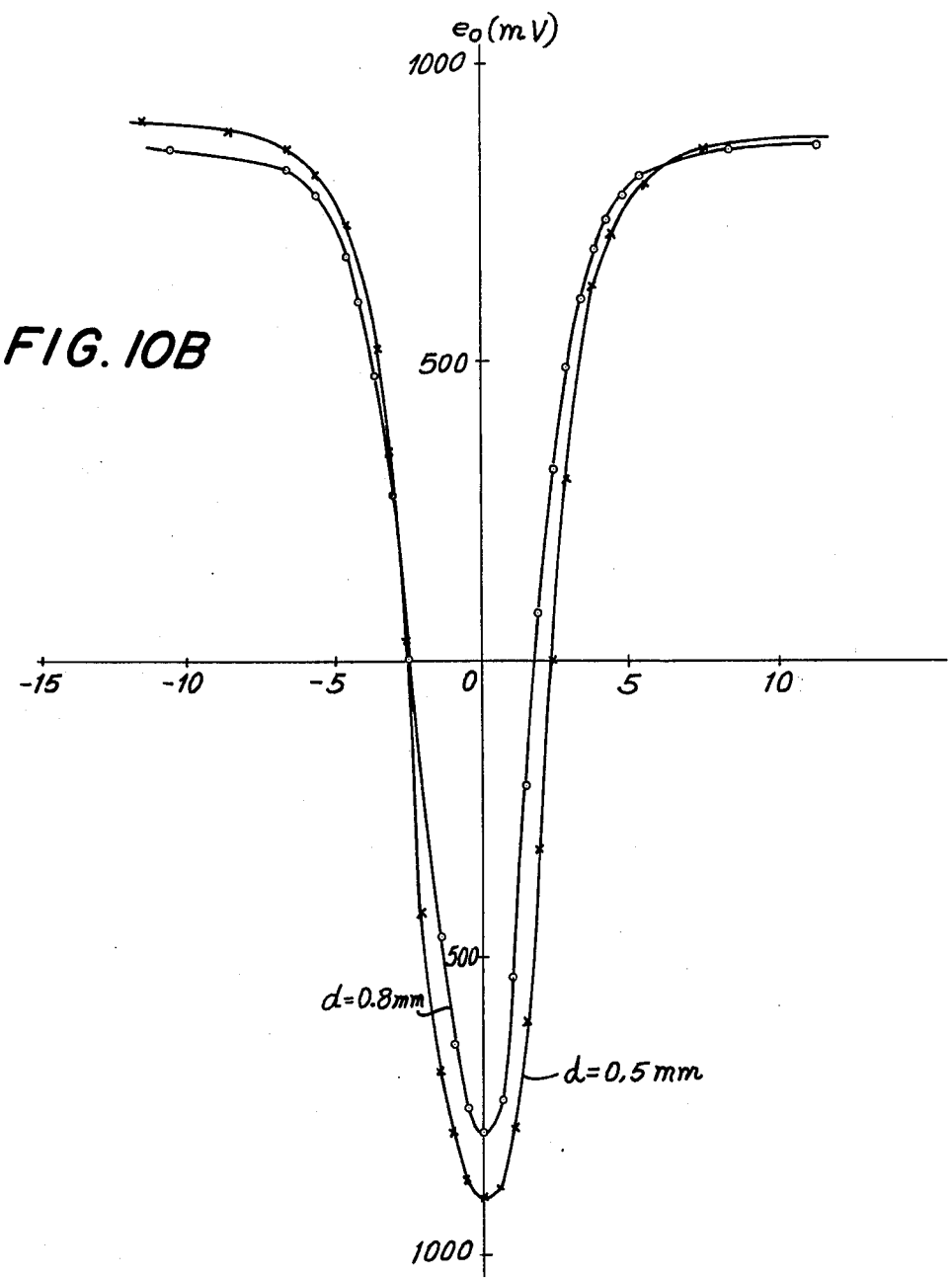

Another example of the use of detector 10 as a proximity detector is shown in FIG. 10A, with the characteristic curves for this example being of the type shown in FIG. 10B. The bias magnet in this example may be of barium ferrite. The dimensional parameters of the detector are the same as those assumed for the example shown in FIG. 9A. The member 13, whose proximity is sensed by the detector 10, here is cylindrical in shape, having a diameter D and a length L. As in the example of FIG. 9A, the member 13 is formed of soft iron and the outer surface thereof is spaced from the detector by the distance d. Whereas the member 13 in FIG. 9A is moved in the x direction along its longitudinal axis, the member 13 in FIG. 10A is moved in the x direction perpendicular to its longitudinal axis.

When the member 13 is moved to pass in front of the detector 10, that is, it passes in front of and across the north pole face (N) of the bias magnet, the resultant output signal $e_o$ which is derived from the magnetoresistive element is related to the proximity of the member as shown by the characteristic curves of FIG. 10B for the conditions wherein d is equal to 0.5mm and 0.8mm, respectively. Because of the cylindrical shape of the member 13, there is no region of constant field $H_2$ in the member, as was true for the rectangular shape shown in FIGS. 9A–9B. This is depicted in FIG. 10B which shows that a maximum peak value of the output voltage is attained when the member is moved in the x direction until its diameter is aligned with the detector 10. It is appreciated that the origin for the curves of FIG. 10B is selected to correspond to this alignment, whereat magntically permeable material is closest to the detector. Thus, maximum flux produced by the bias magnet is intercepted by the cylindrical member of FIG. 10A only when the longitudinal axis of the member is aligned with the detector; while maximum flux is intercepted by a member having a planar surface (as in FIG. 9A) over a substantial length of that member. This is represented by the curves of FIGS. 10B and 9B, respectively.

A consideration of the curves of FIG. 9B and the curves of FIG. 10B indicates that it is preferable for the dimension of the member 13 that is parallel to the x direction, i.e., the direction along which it moves, to be greater than the total thickness of the detector 10. If this dimension of the member is on the same order as the thickness of the detector, less flux will be intercepted by the member and, therefore, the field $H_1$ due to the bias magnet will not be significantly affected. Consequently, the angle $\theta$, as shown in FIG. 6, will be small because the field $H_2$ will be small, and the sensitivity of the detector is not fully exploited. Also, if the plane of the magnetoresistive element is parallel to the longitudinal dimension of the member 13, for example, if the plane of the element is parallel to the facing surface of the member in FIG. 9A, the influence on the field $H_1$ passing through the element by the permeable material of the member is not very great. This too reduces the sensitivity of the detector. Accordingly, although these configurations are operative, they are not preferred in many applications.

Figure 11A:
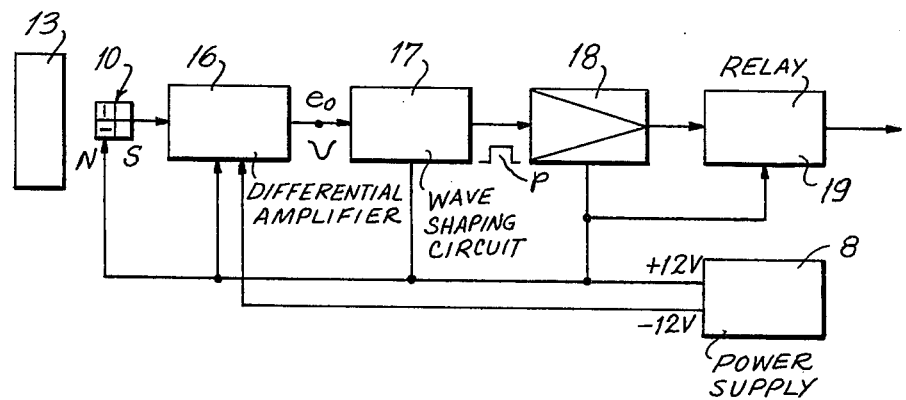
FIGS. 11A and 11B schematically depict how the present invention can be used as a contactless switch.
Figure 11B:
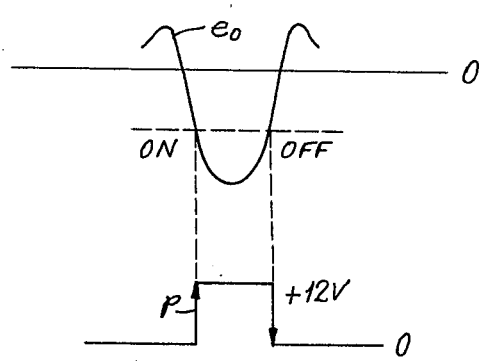

The use of the detector 10 in combination with the member 13 to thus perform the function of a contactless switch now will be described with reference to FIGS. 11A and 11B. As shown in FIG. 11A, the configuration between the detector and the member formed of material having high magnetic permeability may be of the type previously described with respect to FIG. 6. The output of the magnetoresistive element is coupled to a differential amplifier 16 which, for example, may also include the bridge circuit resistors $R_1$ and $R_2$. The output of the differential amplifier is supplied through a wave shaping circuit 17 and an additional amplifier 18 to an actuating device 19. A power supply 8 is shown as being coupled to all of the circuit elements for the purpose of energizing same.

The actuating device 19 preferably comprises an indicating circuit for the purpose of indicating the positional relation between the member 13 and the detector 10. As one example thereof, the indicating circuit 19 may comprise a relay.

In operation, as the member 13 moves linearly along a path past the detector 10, as shown, for example, in FIGS. 6, 8 or 9A, the signal produced by the magnetoresistive element is supplied to the differential amplifier 16 whereat the output signal $e_o$ is generated. For convenience, the output signal $e_o$ is graphically depicted in FIG. 11B. The output signal $e_o$ is supplied to the wave shaping circuit which, preferably, comprises a threshold detector. Any conventional threshold detector can be used, such as Schmitt trigger, or the like, such that when the level of the output signal $e_o$ traverses the predetermined threshold level, as represented by the broken line in FIG. 11B, an output pulse is produced. This output pulse $p$ is further amplified by amplifier 18 and applied to the relay 19. In this example, the positive transition of the output pulse $p$ is used to turn the relay 19 on, and the negative transition of the output pulse is used to turn the relay off. Of course, if desired, the relay can be such whereby it is energized in response to a negative transition and de-energized in response to a positive transition. In that event, the pulse $p$, as shown in FIG. 11B, will be inverted.

As is recognized, the selective actuation of the relay 19 can be used to perform any suitable switching function, as desired. Hence, the circuit arrangement of FIG. 11A functions as a contactless switch whereby the switching function is performed without the actual, physical contact of switching contacts by, for example, a mechanical element.

Figure 12:
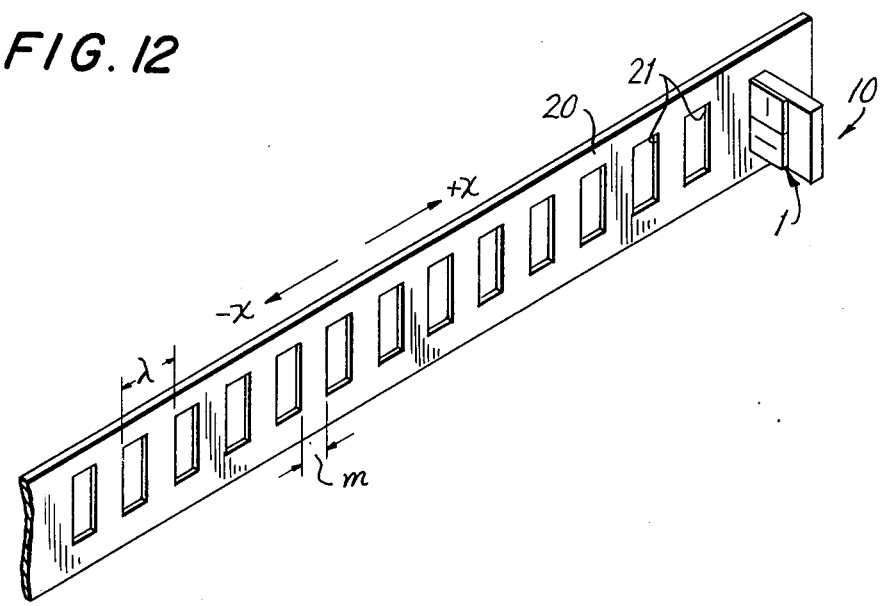

Another application of the present invention is depicted in FIG. 12. In this application, the detector 10, in combination with a strip of material having relatively high magnetic permeability and being provided with uniformly spaced areas of non-magnetic material, such as apertures, functions as a speed detector, a length detector, or the like. The strip 20 may be formed of soft iron or permalloy and is adapted to move in the $\pm x$ direction, as indicated. The strip may be coupled to, mounted upon or driven by other apparatus whose movement is to be sensed. The areas of non-magnetic material, such as apertures 21, provided in the strip 20 preferably are of square or rectangular configuration and may be formed by conventional techniques such as stamping, photo-etching, and the like. As shown, the apertures 21 are uniformly spaced along the length of the strip 20 and are periodic so as to define one period $\lambda$. Adjacent apertures are separated by magnetically permeable material having a width $m$.

The detector 10 is spaced from the strip 20 by the distance $d$. As the strip is moved longitudinally, magnetically permeable material and apertures alternately pass in front of the detector. It now should be appreciated that when the center line of a width of material $m$ is aligned with the detector 10, maximum flux is intercepted, resulting in a field $H_2$ having maximum strength. Conversely, when the center line of an aperture 21 is aligned with the detector, minimum flux is intercepted by the magnetically permeable strip to thus induce a field $H_2$ of minimum strength. Thus, as the field $H_2$ varies with the movement of the strip, the output signal derived from the magnetoresistive element also varies. If this output signal is supplied to the circuit shown in FIG. 8 or to the circuit shown in FIG. 11A, a train of output pulses is produced having a frequency proportional to the aperture period $\lambda$ and the speed of movement of the strip 20. Each pulse represents an increment of movement of the strip and the total number of pulses which are produced represents the distance over which the strip is displaced. This number can be used as an indication of strip length. Also, the pulse frequency can be used as an indication of strip speed.

If desired, the output pulses can be supplied to further apparatus, such as a computer, counter, frequency detector or other pulse signal processing apparatus.

Figure 13:
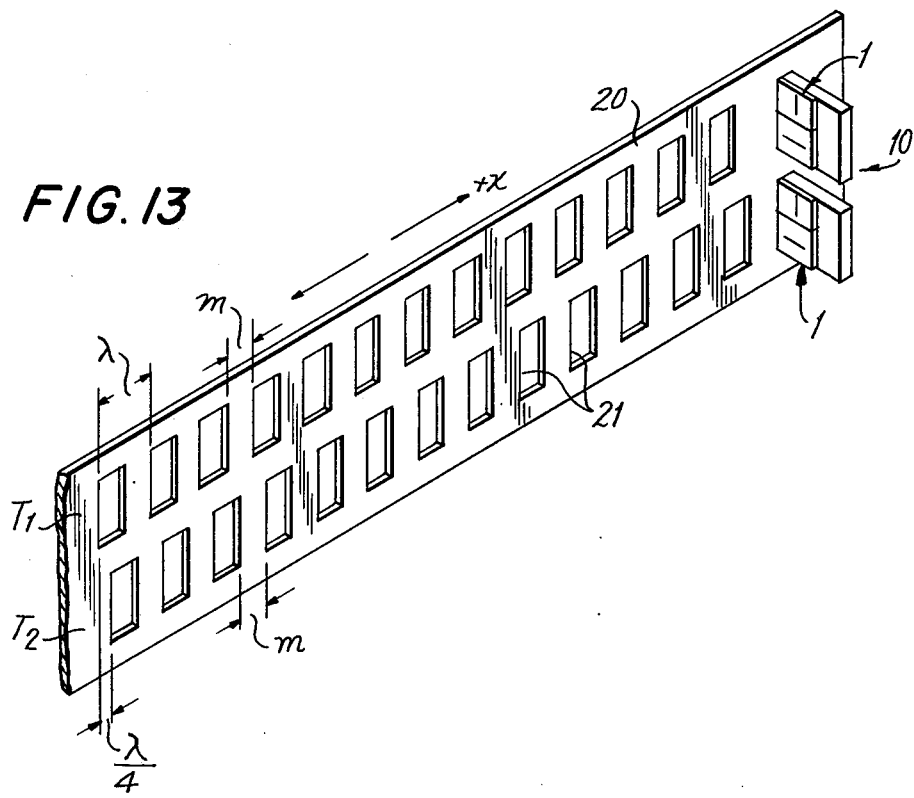

Although the embodiment shown in FIG. 12 can be used to determine length or speed of movement of the strip 20, the output pulses, by themselves, do not indicate whether the strip is moved in the $+x$ direction or in the $-x$ direction. By providing another row or track of areas of non-magnetic material, or apertures, as shown in FIG. 13, the direction of strip movement can be determined. This second track $T_2$ of apertures is offset from the first track $T_1$ by, for example, one-fourth the period of spaced apertures, or $\lambda/4$. Alternatively, this offset can be $\lambda/8$. Now, if individual detectors are provided for the respective tracks $T_1$ and $T_2$, one detector will produce an output signal in phase leading (or lagging) relation with respect to the other detector. That is, if the strip is moved in the $-x$ direction and if the apertures in both tracks are of equal width and spacing, then the output pulses which are derived from the respective detectors will have equal frequencies and duty cycles, but the phase of the pulses which are produced by sensing the track $T_1$ will lead the pulses which are produced by sensing the track $T_2$. Conversely, if the strip 20 is moved in the $+x$ direction, the phase of the pulses which are produced by sensing the track $T_2$ will lead the pulses which are produced by sensing the track $T_1$. Suitable apparatus can be coupled to the detectors to utilize this direction information.

Figure 14:
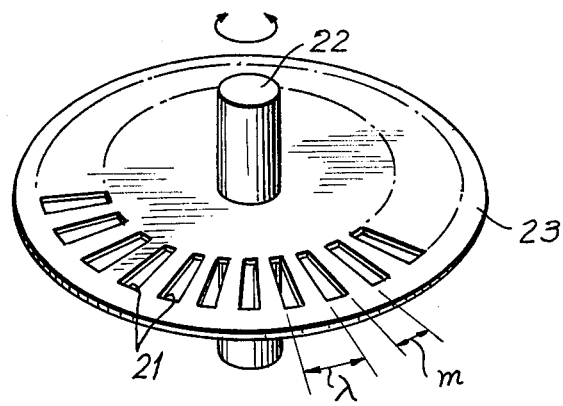

The embodiment depicted in FIG. 12 to sense linear motion and velocity can be modified to sense angular motion and velocity. This is represented in FIG. 14 wherein a disc 23 of magnetically permeable material is mounted on a shaft 22 and is adapted for rotary motion. Areas of non-magnetic material, such as apertures 21, are provided circumferentially about the disc and are uniformly spaced apart to define the period $\lambda$; adjacent apertures being separated by a width m of permeable material. If a detector 10 (not shown) is placed above, or below, the disc 23 adjacet the circumferential path of the apertures 21, output pulses can be derived from the detector having a frequency proportional to $\lambda$ and to the rotary speed of the disc. Thus, similar to the linear motion detector of FIG. 12, an angular motion detector is obtained. This angular motion detector can be used as a shaft encoder or for other purposes, as desired.

Figure 15:
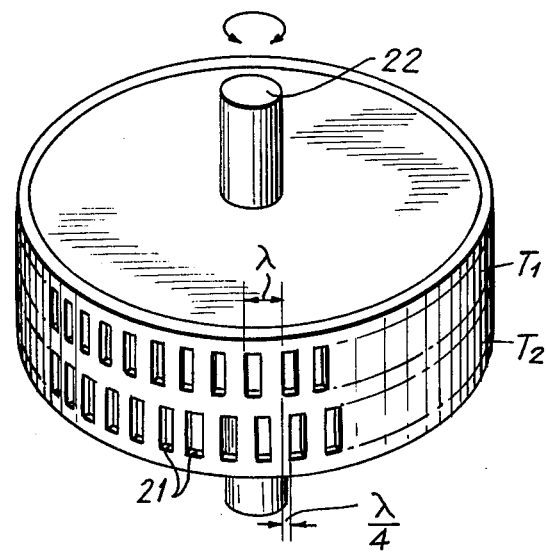

A modification of the angular motion detector of FIG. 14, to enable the direction of rotation to be determined, is shown in FIG. 15. In this modified embodiment, two tracks $T_1$ and $T_2$ of offset areas of non-magnetic material, or apertures, are provided. Since this embodiment is similar to the previously described embodiment of FIG. 13, further description thereof need not be provided. One of ordinary skill in the art will readily appreciate how direction information is attained from this illustrated embodiment.

Figure 16:
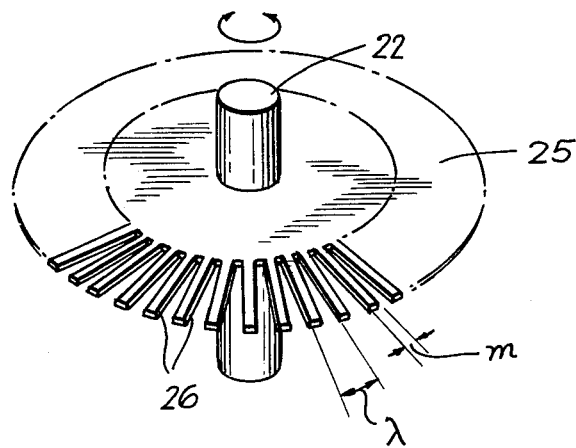

A further embodiment of an angular motion detector is shown in FIG. 16 and comprises a disc or ring 25 mounted on a shaft 22 and adapted for rotary motion. The disc or ring is provided with uniformly spaced teeth 6 which define a period $\lambda$. The teeth are of a highly permeable material having a width m. It is appreciated that the disc or ring can be formed of permeable material and the teeth are stamped therefrom. Alternatively, the disc can be of different material and the teeth may be added to the periphery of the disc. In either embodiment, the angular motion of the teeth is sensed by providing a detector above (or below9 the plane of the disc, juxtaposed the circumferential track defined by the teeth. This is seen to be similar to the angular motion detector described hereinabove with respect to FIG. 14. As another embodiment, the detector (not shown) is spaced from and faces the peripheral boundary defined by the teeth, similar to the motion detector previously described with respect to FIG. 12. Since the angular motion detector which can be formed of the embodiment shown in FIG. 16 is similar in operation to the previously described embodiments of motion detectors, an adequate understanding thereof does not require further description.

Figure 17:
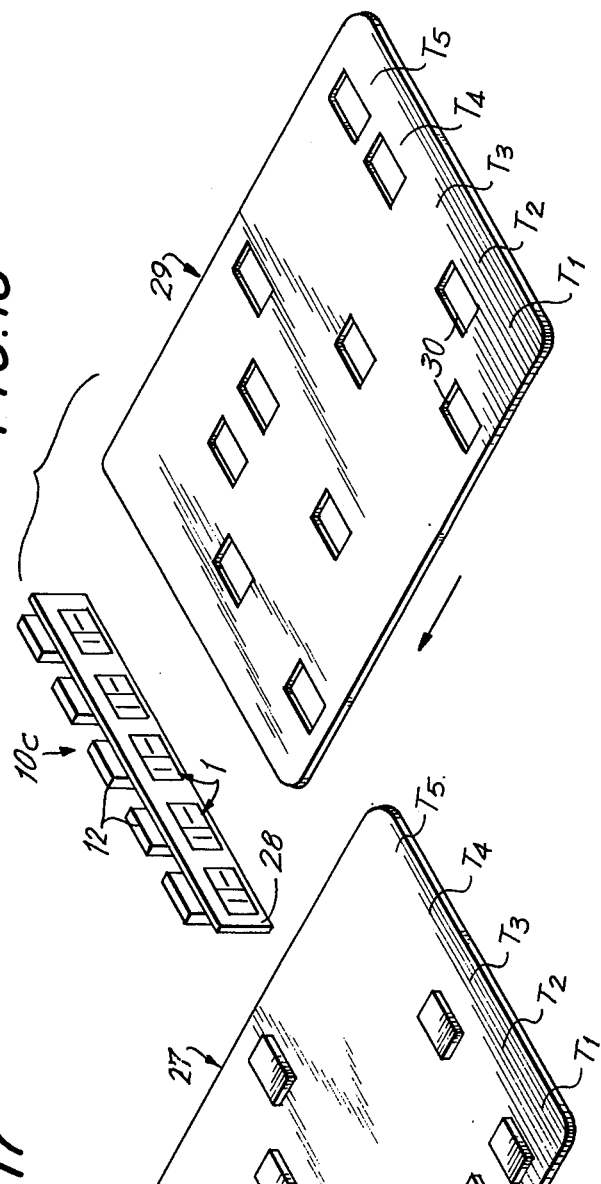
FIGS. 17, 18 and 19 show how the present invention can be used to read out encoded information from, for example, a data card.

A still further application of the present invention is depicted in FIG. 17. As shown therein, a matrix array 10c of detectors is provided on a suitable support 28, preferably of non-magnetic material. Each detector included in the array is comprised of a magnetoresistive element 1 coupled to a bias magnet 12. This array, which is represented as a linear matrix, is capable of reading out selective bits of information represented by an array of members 13 of highly permeable material which are selectively positioned on a suitable support 27. As one example thereof, the support 27 may comprise an information card and the members 13 may be selectively positioned in columns (or rows) $T_1, T_2, \ldots T_5$ to represent information on that card. The support is formed of non-magnetic material.

Each detector included in the array 10c is aligned with a corresponding one of the columns $T_1 \ldots T_5$. Hence, if the support 27 is moved past the detectors in the direction of the arrow, or if the detectors pass over the support in an opposite direction, the flux produced by certain ones of the bias magnets will be intercepted by the permeable members disposed in the corresponding columns, to alter the bias fields therein, whereby the vectorially combined fields change the direction of the fields passing through corresponding magnetoresistive elements, in the now understood manner. Hence, output signals are derived from selected detectors, depending upon whether a permeable member is sensed during the relative displacement of the support 27 and the detector array 10c. These output signals can be used to represent the information which is encoded on the support, and may be supplied to suitable processing apparatus, such as a computer, printer, central processor, or the like.

Figure 18:
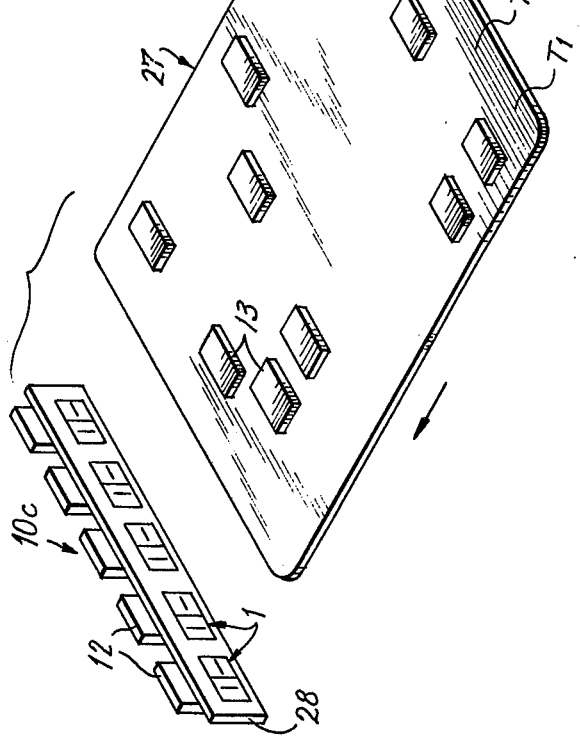

A modification of the information card shown in FIG. 17 is depicted in FIG. 18 wherein the support 29 is of highly permeable material and the information thereon is represented by selected apertures 30. Thus, the information representing bits and support therefor in FIG. 14 are, essentially, interchanged in FIG. 18. Nevertheless, the array of detectors 10c is substantially the same and a similar technique is used to obtain and utilize the information which is encoded on the support 29. Hence, in the interest of brevity, further description of the FIG. 18 embodiment is not provided. It is appreciated that the selected presence (or absence) of an aperture in a column and row on the information card is represented by a corresponding change in the output signal derived from the detectors.

While the foregoing description has assumed that there is relative displacement between the linear array of detectors 10c and the information card, an alternative embodiment comprises an nxm array of detectors corresponding to the nxm members (or apertures) on the information card. The outputs of all of the detectors in a column $T_1 \ldots T_5$ are connected in common to, for example, a differential amplifier or other output device; and the current supply terminals 7A and 7B of a row of detectors are connected to an associated current supply input. To read out the encoded information on a properly positioned data card, the respective current supply inputs are actuated in sequence to permit successive rows of detectors to sense the presence (or absence) of members or apertures. In this manner, the encoded information is read out on a row-by-row basis.

Figure 19:
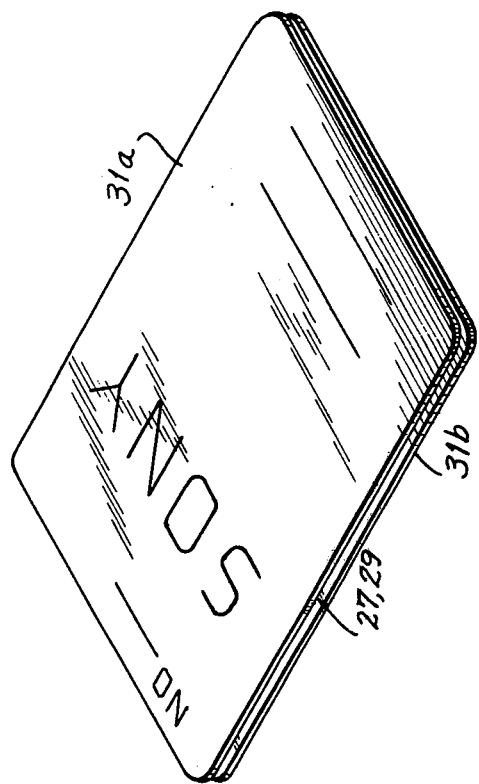

An embodiment of a suitable information card embodying the examples of FIGS. 17 and 18 is shown in FIG. 19. This information card can be used as an identification card, a credit card, or the like. The data-bearing support 27 or 29 is sandwiched between non-magnetic members 31a and 31b which may serve additionally to protect and shield the data support.

Figure 20:
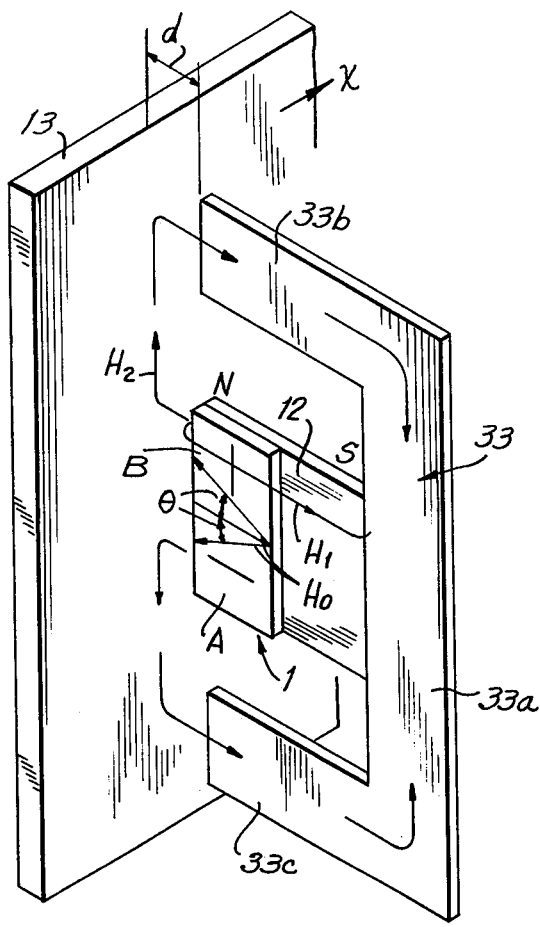
FIG. 20 shows another embodiment of the present invention.

A still further embodiment of a detector 10 is illustrated in FIG. 20 and is comprised of a magnetoresistive element 1 mounted on a bias magnet 12 magnetized in its longitudinal direction and juxtaposed the permeable member 13. The bias magnet 12 is in magnetic communication with a yoke 33 having arms 33b and 33c interconnected by a leg 33a. The yoke is of material having a relatively high magnetic permeability such as permalloy, and provides a good flux path.

The bias field $H_1$ which is generated by the magnet 12 results in a field component $H_2$ in the member 13. Thus, a magnetic circuit is formed between the north pole (N) and the south pole (S) of the magnet by the path comprising the member 13, the arm 33b and the leg 33a of the yoke. A parallel path comprises the member 13, the arm 33c and the leg 33a. It is appreciated that, by providing the highly permeable yoke 33 in the flux path, there is less flux leakage and, therefore, a stronger field $H_2$. This, in turn, increases the sensitivity of the detector because the angle $\theta$ formed by the vector combination of the bias field $H_1$ and the field $H_2$ is permitted to exhibit a larger range.

Figure 21:
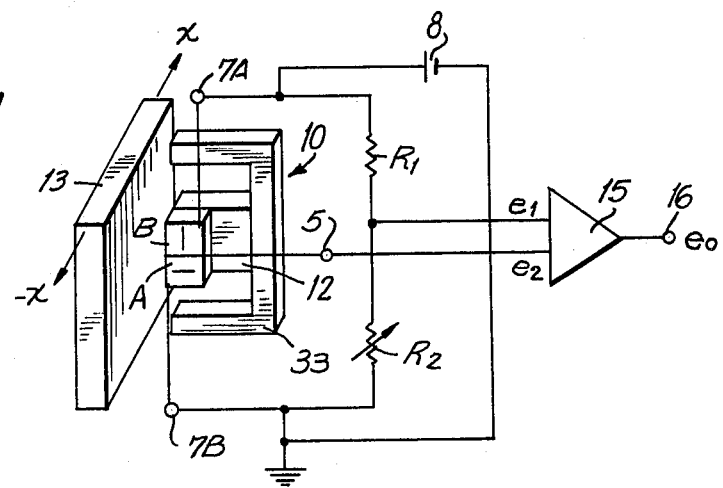
FIG. 21 shows one embodiment of signal processing apparatus which can be used with the embodiment of FIG. 20.

FIG. 21 is a schematic circuit diagram showing how the detector of FIG. 20 can be used to produce an output signal $e_0$ as an indication of the movement of the member 13. Since this circuit is similar to the aforedescribed circuit shown in FIG. 8, further description thereof is not necessary for an understanding of its construction and operation.

Although the present invention has been particularly shown and described with reference to certain ones of the preferred embodiments, it is contemplated that various changes and modifications in form and details may be made. As one example, if the ferromagnetic film strips A and B which comprise the magnetoresistive element 1 do not have identical characteristics, suitable compensation nevertheless can be obtained. That is, when the ferromagnetic strips A and B are deposited on the substrate, the magnetic particles in the film initially should be magnetically oriented in the proper direction. This magnetic orientation during deposition on the substrate will assure substantially identical characteristics of the strips A and B.

As another example, temperature compensation of the magnetoresistive element can be provided. One embodiment of such temperature compensation employs two magnetoresistive elements connected in bridge circuit configuration, as described in greater detail in copending application Ser. No. 597,007.

Therefore, it should be understood that the appended claims are to be interpreted as including all of such changes and modifications, as well as various other types of application for which the present invention is particularly well suited.

What is claimed is:

1. Apparatus for producing an output signal upon sensing the proximity of a member having material of a relatively high magnetic permeability, comprising:
    magnetoresistive element means comprised of an insulating substrate and perpendicularly disposed ferromagnetic strips on said substrate for providing first and second main current conducting paths between a pair of current supply terminals, said strips being connected in series to define a junction therebetween from which an output signal is derived;
    a bias magnet for providing a bias magnetic field which passes through said magnetoresistive element means, said magnetoresistive element means being mounted on said bias magnet, and said bias magnetic field having at least a component which is parallel to said substrate in a direction perpendicular to one of said strips; and
    a member having material of a relatively high magnetic permeability and adapted to be disposed in the vicinity of said magnetoresistive element means to receive a portion of said bias field so as to alter the distribution of said received bias field, whereby a composite magnetic field passes through said magnetoresistive element means in a direction dependent upon the proximity of said member to thereby produce said output signal.

2. Apparatus according to claim 1 wherein said member has a surface which is substantially perpendicular to said substrate.

3. Apparatus according to claim 1 wherein the altered distribution of said received bias magnetic field is substantially perpendicular to said bias field passing through said magnetoresistive element means.

4. Apparatus according to claim 1 wherein said member is movable in a direction perpendicular to said substrate.

5. Apparatus according to claim 1 wherein a pole of said bias magnet is in facing relation to said member; and said composite field is at an angle with respect to a main current conducting path and is of an intensity sufficient to saturate said magnetoresistive element means.

6. Apparatus according to claim 1 further comprising output circuit means coupled to said junction for producing an output representation of said output signal derived at said junction.

7. Apparatus according to claim 6 wherein said output circuit means comprises impedance means connected in parallel with said series-connected strips to thereby form a bridge circuit with said strips; and a differential amplifier having a first input terminal coupled to said junction and a second input terminal coupled to said impedance means.

8. Apparatus according to claim 7 wherein said output circuit means further comprises threshold detecting means coupled to said differential amplifier for detecting when the output from said differential amplifier traverses a predetermined threshold level; and means for indicating the traversal of said predetermined threshold level.

9. Apparatus according to claim 8 wherein said means for indicating comprises relay means actuated in response to the traversal of said predetermined threshold level by said differential amplifier output.

10. Apparatus according to claim 1 wherein said magnetoresistive element means comprises an array of elements, each having an insulating substrate, and perpendicularly disposed ferromagnetic strips on said substrate for providing first and second main current conducting paths between a pair of current supply terminals, said strips being connected in series to define a junction therebetween, each element being mounted on a respective bias magnet; and said member comprises a support having said material of high magnetic permeability disposed thereon in a predetermined pattern.

11. Apparatus according to claim 10 wherein said support is of non-magnetic material having a matrix array of selectively positioned individual members of relativley highly permeable material thereon.

12. Apparatus according to claim 10 wherein said support is of relatively highly permeable material having a matrix array of selective areas of non-magnetic material thereon.

13. Apparatus according to claim 12 wherein said areas of non-magnetic material are apertures.

14. Apparatus according to claim 10 wherein said array of elements is a linear array disposed for relative movement with respect to said member so that each said element senses the presence or absence of said material of high magnetic permeability.

15. Apparatus according to claim 1 wherein said member comprises a strip of material having relatively high magnetic permeability adapted to be linearly displaced and having uniformly spaced areas of non-magnetic material longitudinally disposed thereon; and said magnetoresistive element means is disposed to sense the selective presence of said areas and said permeable material.

16. Apparatus according to claim 1 wherein said member comprises rotatable material having relatively high magnetic permeability; and said magnetoresistive element is disposed to sense said material.

17. Apparatus according to claim 16 wherein said rotatable material is provided with uniformly spaced areas of non-magnetic material separated by areas of material having relatively high magnetic permeability.

* * * * *